United States Patent
Beg et al.

(10) Patent No.: US 10,249,390 B2
(45) Date of Patent: Apr. 2, 2019

(54) METHOD FOR DETERMINING A PROACTIVITY SCORE FOR HEALTH

(71) Applicants: Sami A. Beg, Greenville, NC (US); Sumyra Kachru, Greenville, NC (US); M. Ashraf Beg, Anantnag (IN); Naseema Anjum, Anantnag (IN)

(72) Inventors: Sami A. Beg, Greenville, NC (US); Sumyra Kachru, Greenville, NC (US); M. Ashraf Beg, Anantnag (IN); Naseema Anjum, Anantnag (IN)

(*) Notice: Subject to any disclaimer, the term of this patent is extended or adjusted under 35 U.S.C. 154(b) by 0 days.

(21) Appl. No.: 14/571,246

(22) Filed: Dec. 15, 2014

(65) Prior Publication Data
US 2015/0164399 A1 Jun. 18, 2015

Related U.S. Application Data (60) Provisional application No. 61/915,523, filed on Dec. 13, 2013.

(51) Int. Cl.
| | |
|---|---|
| G16H 50/30 | (2018.01) |
| G06Q 10/10 | (2012.01) |
| G06Q 50/22 | (2018.01) |
| G06F 19/00 | (2018.01) |

(52) U.S. Cl.
CPC ............ *G16H 50/30* (2018.01); *G06F 19/00* (2013.01); *G06Q 10/10* (2013.01); *G06Q 50/22* (2013.01)

(58) Field of Classification Search
None
See application file for complete search history.

(56) References Cited

U.S. PATENT DOCUMENTS

| | | | | |
|---|---|---|---|---|
| 2007/0185391 A1* | 8/2007 | Morgan | ............... | A61B 5/0002 600/301 |
| 2008/0126124 A1* | 5/2008 | Schechter | ........... | G06F 19/3431 705/2 |
| 2011/0184250 A1* | 7/2011 | Schmidt | ................. | G06Q 10/00 600/300 |
| 2014/0303988 A1* | 10/2014 | Maneri | ................. | G06F 19/345 705/2 |

OTHER PUBLICATIONS

J. Reckelhoff, Gender differences in the regulation of blood pressure, Hypertension. May 2001; 37(5):1199-208.*
Basu et al, Effects of Age and Sex on Postprandial Glucose Metabolism, Diabetes, vol. 55, Jul. 2006, pp. 2001-2014.*
Ranasinghe et al, Relationship between Body mass index (BMI) and body fat percentage, estimated by bioelectrical impedance, in a group of Sri Lankan adults: a cross sectional study, BMC Public Health 2013, 13:797, published online on Sep. 3, 2013.*

* cited by examiner

*Primary Examiner* — Carl H Layno
*Assistant Examiner* — Qingjun Kong
(74) *Attorney, Agent, or Firm* — Kanika Radhakrishnan; Evergreen Valley Law Group (57) ABSTRACT

A method for measuring a health proactivity status of a human is disclosed. The method includes obtaining multiple physical characteristics associated with the human, generating a health-related metric based upon the characteristics, periodically obtaining the multiple characteristics associated with the human, periodically generating the health-related metric based upon the periodically obtained characteristics, comparing the periodically generated health-related evaluations to determine change over the course of a defined time, and dynamically determining an overall proactivity score for health of the human based upon the comparisons.

17 Claims, 10 Drawing Sheets

| (Sample points; max 1000; score never exceeds 1000 even with adjustment factors) | Optimal | Near Optimal | Not Optimal | | | | Not Done (Follow up in subsequent year not completed) | Not Done (Ever) |
|---|---|---|---|---|---|---|---|---|
| | | | Improvement | | No Improvement | | | |
| | | | Metric Met | Metric Missed | Same | Worse | | |
| *Points allocated based on reevaluation | 900 | 800 | 700 | 500 | 300 | 200 | 100 | 0 |

FIG. 10

METHOD FOR DETERMINING A PROACTIVITY SCORE FOR HEALTH

CROSS-REFERENCE TO RELATED APPLICATIONS

This application claims the benefit of U.S. Provisional Application No. 61/915,523 filed Dec. 13, 2013 which is hereby incorporated herein by reference in its entirety.

TECHNICAL FIELD

This disclosure relates to health assessment, and more particularly to determining a universal dynamic metric for an individual's proactivity related to their health.

BACKGROUND

The statements in this section merely provide background information related to the present disclosure and may not constitute prior art.

Obesity is an epidemic within the United States and an increasing problem throughout the world. Currently, however, healthcare providers are required to treat individuals on a reactive basis. Most often, treatment is ordered subsequent to diagnosis and development of serious health conditions when it is too late to reverse the damage. Failure to proactively predict or identify health risks can inefficiently incur high health expenses and over utilize our often scarce health-based resources.

Healthcare costs are reduced as individuals reach a healthier weight. Better nutrition and improved physical activity can lead to weight loss which leads to decreased health risks and improved health outcomes. Individuals who are motivated to improve their health through lifestyle management often keep track of their health progress and diet.

Those who take an active role in their health are often rewarded for their efforts. Many employers have implemented programs that reward employees, but these programs are often expensive and fail to meaningfully engage across different jobs and platforms. Given that health data is not consolidated and not standardized, the need for a universal metric that links to the underlying health factor, namely excess weight or obesity, can help transform the way lifestyle management is encouraged in individuals if this is done by providing a dynamic score that is high not only for reaching an optimal range but also for making the right decisions when it comes to weight management, such as showing improvement over time, similar to a credit score which is high for properly managing ones credits, bills and more.

Conventional methodologies concentrate on health metrics which cannot be shared due to Health Insurance Portability and Accountability Act ("HIPAA") and typically use a static health score that indicates the individual's health status at the time of measurement, or with minor modifications around this theme. These conventional metrics lack the ability to generate a dynamic HIPAA compliant metric with no personal health information attached on which everyone from the individual to the marketplace itself can make decisions. The lack of a well-defined and easy to use and understand validated score leads to a "one size fits all" approach to helping individuals understand and benefit from lifestyle management.

Such a metric for the health and related sectors designed in the same way as a credit score is for the financial sector can transform the fight against obesity, helping reduce the direct morbidity and mortality related to it. Furthermore, such a metric will have numerous other applications in the health sector, like identifying and following at risk patients, providing health insurance premium discounts, determining life insurance premiums, as well as other fields impacted by obesity and associated risks. Gamification of the concept can also lead individuals to compete with each other to improve their overall health. Further simplifying and streamlining of the concept and finding innovative ways to operationalize it can lead to its seamless use across multiple platforms, entities and industries. Accordingly, there exists a need for such a method and associated technology applications that cures the current deficiencies and transforms the industry by providing a dynamic score for an individual's health.

SUMMARY

A method for measuring health proactivity of a human is disclosed. The method includes obtaining multiple physical characteristics associated with the human, generating a health-related metric based upon the characteristics, periodically obtaining the multiple physical characteristics associated with the human, periodically generating a health-related metric based upon the periodically obtained characteristics, comparing the periodically generated obesity-related evaluations to determine change over the course of a defined time, and dynamically determining an overall proactivity score for health of the human based upon the comparing.

This summary is provided merely to introduce certain concepts and not to identify key or essential features of the claimed subject matter.

BRIEF DESCRIPTION OF THE DRAWINGS

One or more embodiments will now be described, by way of example using obesity-related health metrics, with reference to the accompanying drawings, in which.

DETAILED DESCRIPTION

Various embodiments of the present invention will be described in detail with reference to the drawings, where like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

As used in the description herein and throughout the claims, the following terms take the meanings explicitly associated herein, unless the context clearly dictates otherwise: the meaning of "a," "an," and "the" includes plural reference, the meaning of "in" includes "in" and "on."

Figure 1:
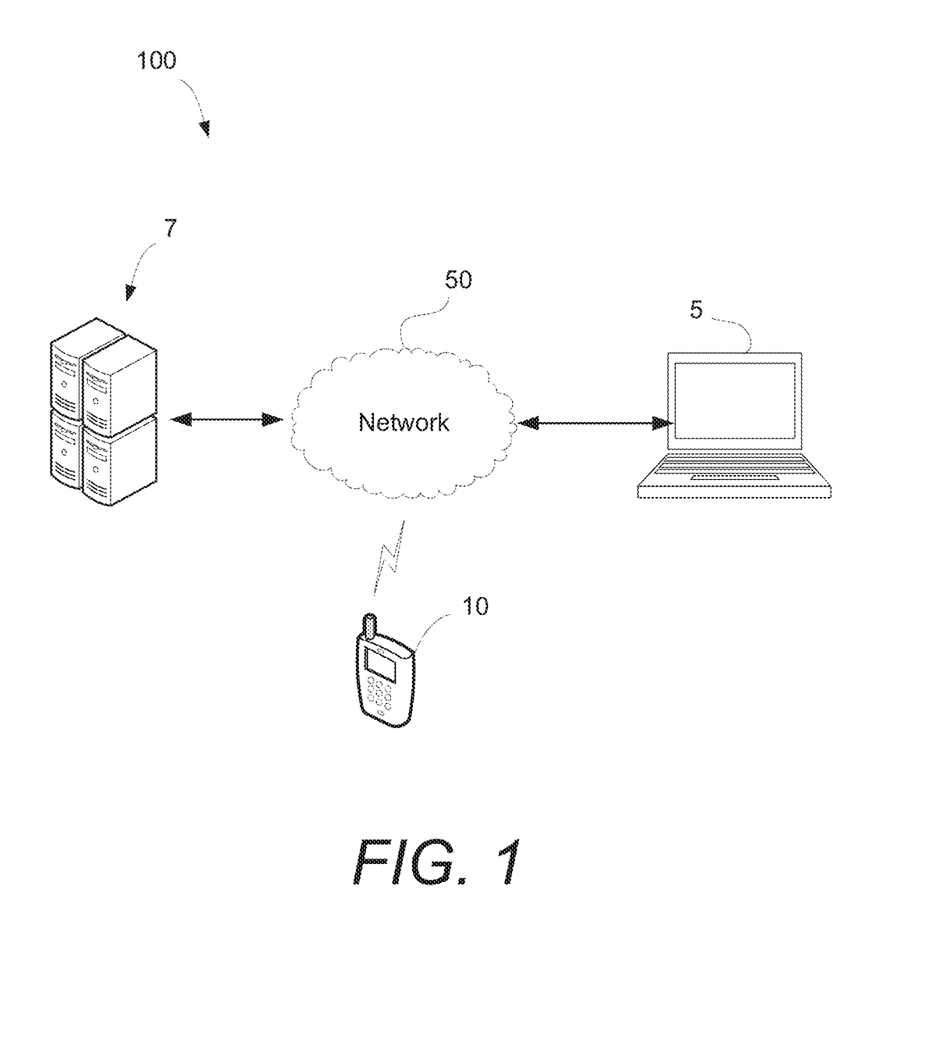
FIG. 1 is a block diagram of an overview of the health assessment system, in accordance with the present disclosure.

Referring now to the drawings, wherein the depictions are for the purpose of illustrating certain exemplary embodiments only and not for the purpose of limiting the same, FIG. 1 schematically shows an exemplary score generating system 100 that may help implement the methodologies of the present disclosure. The system 100 includes a server system 7 and may include any number of computing devices 5 and mobile devices 10 connected through a network 50. The server system 7 may be communicatively connected to the computing device 5 and the mobile device 10 via the network 50. The mobile device 10 may be physically connected to the network 50 or the computing device 5 during selected periods of operation without departing from the teachings herein. Components of the system 100 are shown in FIG. 1 as single elements. Such illustration is for ease of description and it should be recognized that the system 100 may include multiple additional mobile and computing devices.

The network 50 may be any suitable series of points or nodes interconnected by communication paths. The network 50 may be interconnected with other networks and contain sub networks network such as, for example, a publicly accessible distributed network like the Internet or other telecommunications networks (e.g., intranets, virtual nets, overlay networks and the like). The network 50 may facilitates the exchange of data between and among the mobile device 10, the computing device 5, and the server system 7 although in various embodiments the mobile device 10 may be directly connected to the computing device 5.

FIG. 1 is used to provide an overview of the health assessment system 100 in which exemplary embodiments may be used and to provide an overview of an exemplary embodiment of instant disclosure. In FIG. 1, there is a computer system/server 7, which is operational with numerous other general purpose or special purpose computing system environments or configurations. Examples of well-known computing systems, environments, and/or configurations that may be suitable for use with computer system/server 7 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The server system 7 preferably executes database functions including storing and maintaining a database and processes requests from the mobile device 10 and the computing device 5 to extract data from, or update, a database as described herein below. The server 7 may additionally provide processing functions for the mobile device 10 and the computing device 5 as will become apparent to those skilled in the art upon a careful reading of the teachings herein.

The mobile device 10 may include one or more applications that the user may operate. Operation may include downloading, installing, turning on, unlocking, activating, or otherwise using the application. The application may comprise at least one of an algorithm, software, computer code, and/or the like, for example, mobile application software. In the alternative, the application may be a website accessible through the World Wide Web.

Figure 2:
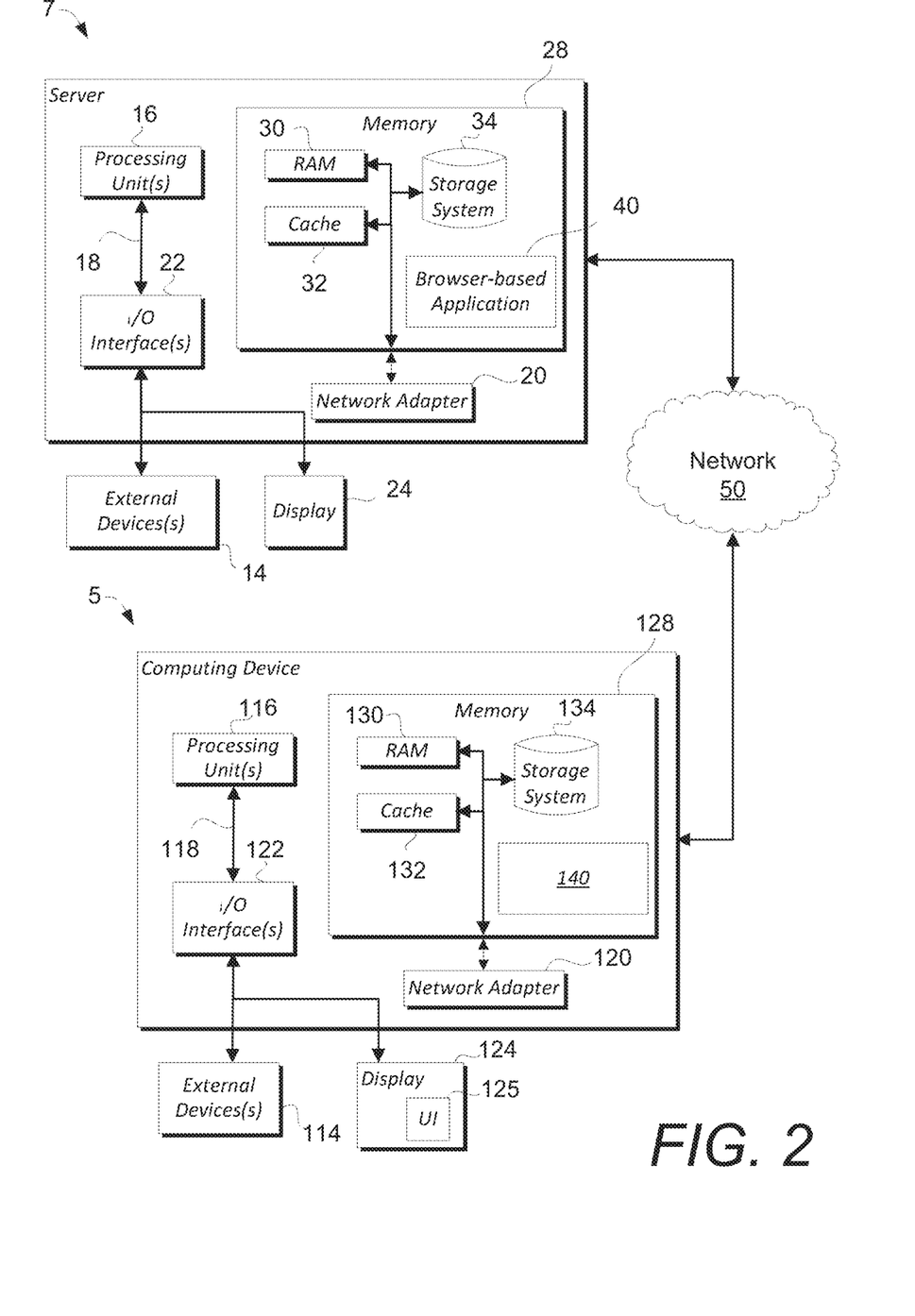
FIG. 2 is a block diagram of an exemplary server and computing device in communication via a network, in accordance with the present disclosure.

FIG. 2 shows a block diagram of the exemplary server 7 and computing device 5 in communication via the network 50. As shown in FIG. 2, computer system/server 7 is shown in the form of a general-purpose computing device. The components of computer system/server 7 may include, but are not limited to, one or more processors or processing units 16, a system memory 28, and a bus 18 that couples various system components including system memory 28 to one or more processing units 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The computer system/server 7 may include a variety of computer system readable media, such as memory 28. Such media may be any available media that is accessible by computer system/server 7, and such media includes both volatile and non-volatile media, removable and non-removable media. System memory 28 can include computer system readable media in the form of volatile memory, such as random access memory (RAM) 30 and/or cache memory 32. Computer system/server 7 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a removable, non-volatile memory, such as a memory card or "stick" may be used, and an optical disk drive for reading from or writing to a removable, non-volatile optical disk such as a CD-ROM, DVD-ROM or other optical media can be provided. In such instances, each can be connected to bus 18 by one or more I/O (Input/Output) interfaces 22.

The computer system/server 7 may also communicate with one or more external devices 14 such as a keyboard, a pointing device, a display 24, etc.; one or more devices that enable a user to interact with computer system/server 7; and/or any devices (e.g., network card, modem, etc.) that enable computer system/server 7 to communicate with one or more other computing devices. Such communication can occur via, e.g., I/O interfaces 22. Still yet, computer system/server 7 can communicate with one or more networks such as a local area network (LAN), a general wide area network (WAN), and/or a public network (e.g., the Internet) via network adapter 20. As depicted, network adapter 20 communicates with the other components of computer system/server 7 via bus 18. It should be understood that although not shown, other hardware and/or software components could be used in conjunction with computer system/server 7. Examples, include, but are not limited to: microcode, device drivers, redundant processing units, external disk drive arrays, redundant array of independent disks (RAID) systems, tape drives, and data archival storage systems, etc.

The computing device 112 also comprises a memory 128, one or more processing units 116, one or more I/O interfaces 122, and one or more network adapters 120, interconnected via bus 118. The memory 128 may comprise non-volatile and/or volatile RAM, cache memory 132, and a storage system 134. Depending on implementation, memory 128 may include removable or non-removable non-volatile memory. The computing device 112 may include or be coupled to the display 124, which has a user-interface (UI) 125. Depending on implementation, the computing device 112 may or may not be coupled to external devices 114. The display may be a touchscreen, flat screen, monitor, television, projector, as examples. The bus 118 may be any bus suitable for the platform, including those buses described above for bus 18. The memories 130, 132, and 134 may be those memories 30, 32, 34, respectively, described above. The one or more network adapters 120 may be wired or wireless network adapters. The I/O interface(s) 122 may be interfaces such as USB (universal serial bus), SATA (serial AT attachment), HDMI (high definition multimedia interface), and the like.

In this example, the computer system/server 7 is connected to the computing device 112 via network 50 and links 51, 52. The computing device 112 connects to the computer system/server 7 in order to access the browser-based application 40. A browser application is, e.g., an application designed to enable users to access, retrieve and view documents and other resources on a network 50 and particularly on the Internet. However, the network 50 may be an internal network such as used in many computing environments, e.g., various business enterprises.

Figure 3:
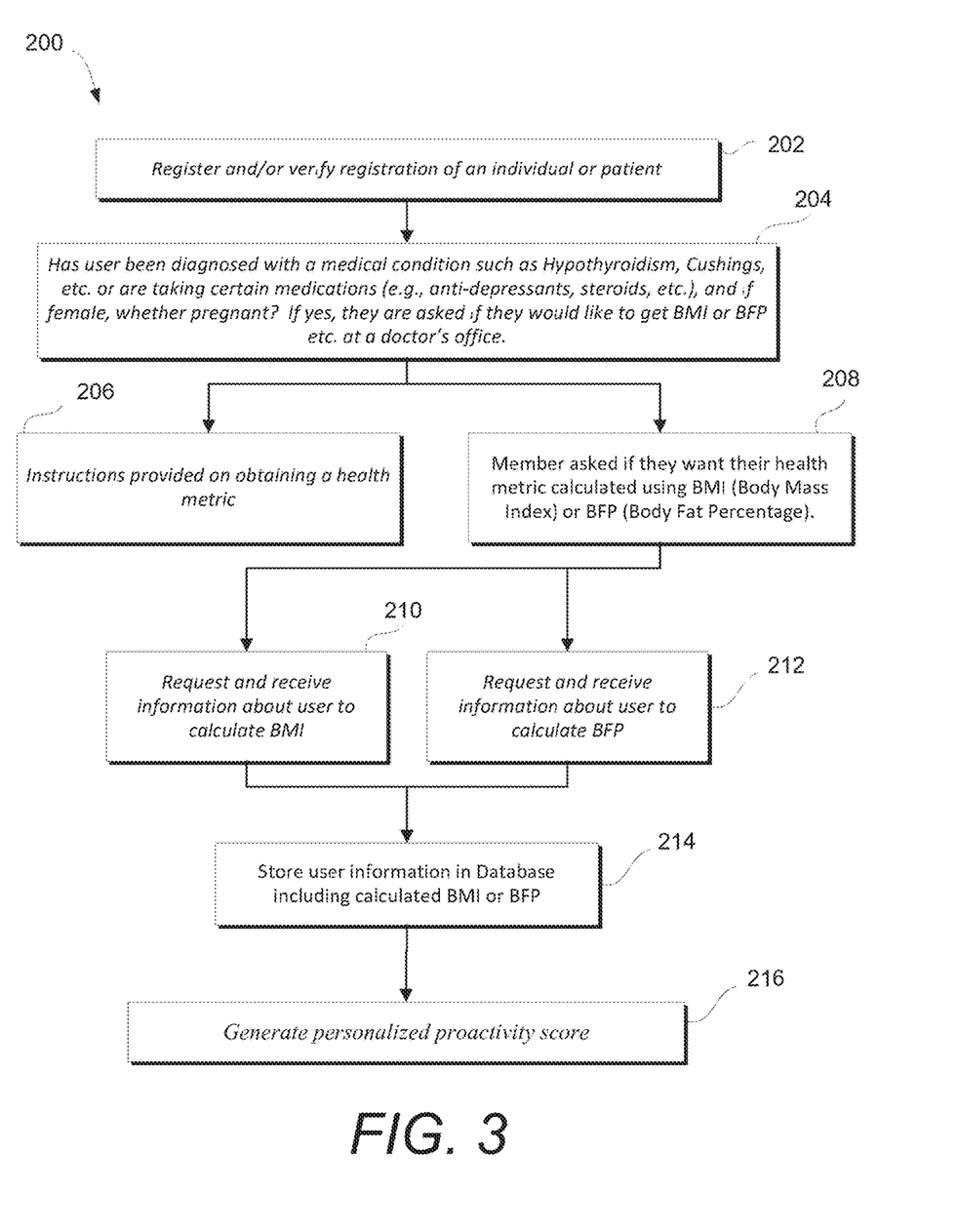
FIG. 3 shows an exemplary overall process for determining an individual's or patient's personalized proactivity score, in accordance with the present disclosure.

FIG. 3 shows an exemplary process for determining an individual's or patient's personalized proactivity score for health. The process and algorithm defined is applicable to any health factor. In the embodiment described herein obesity related metrics such as "body mass index" (BMI) or "body fat percentage" (BFP) are used as examples to provide a score for improvements in weight management over time. The same or similar algorithm can be used for providing proactivity scores for various other health-related factors, such as diabetes management, hypertension management, etc.

The process is initiated at step 202 wherein a user, e.g., an individual or a patient, is registered with the system. Returning user's credentials may be request, received and authenticated at this step. At step 204, various personal health related queries may be made to the user including for e.g., (1) has the user been diagnosed with a medical condition such as Hypothyroidism, Cushings, etc.; (2) is the user currently taking or prescribed certain medications, e.g., steroids. If female, pregnancy related questions may be asked, e.g., are you pregnant? At step 206, in various embodiments, if the user has answered yes to any of these questions they are provided an option to obtain the health metric used to calculate the proactivity score for health at a doctor's office, while as other options include health clubs, fitness clubs etc. If affirmative to the option of a physician's office, the system 100 is configured to request or obtain a physical proximity of the user, e.g., through a postal address, Internet Protocol (IP) address, Global Positioning System (GPS) address, and obtain directions or a list of potential medical providers from which to obtain the health metric. Similarly, options based on proximity as determined by address, zip code, GPS etc. are provided for all health clubs, fitness centers etc. that assesses the individual for the health metric and enters it into the system for calculation of the proactivity score for health.

At step 208, the system inquiries the user's preference on conducting the assessment in terms of a "body mass index" (BMI) or "body fat percentage" (BFP), or other options for assessing weight management such as waist circumference, waist and hip ratio, neck size, skin fold thickness, bio-electric impendence, etc. The term "body mass index" or "BMI" of a human patient is defined as the weight in kilograms divided by the square of the height in meters, such that BMI has units of $kg/m^2$.

In one embodiment, in addition to the direct measure of an obesity metric, such as height/weight for BMI or BFP, waist circumference, waist/hip ratio, neck size, etc., the system 100 also allows selection of other metrics that can also be incorporated into the score around the same algorithm process where points are allocated not only for an optimal range or a near optimal range, but also for showing a defined improvement over a certain period of time, or being close to achieving the improvement metric etc. Such additional metrics that can be included can be health metrics such as Lipid Profile (Low-Density Lipoprotein (LDL), High-Density Lipoprotein (HDL), Triglycerides, very low-density lipoprotein (VLDL)), Fasting Blood Glucose, Haemoglobin A1C, Blood Pressure, or similar measurements that relate to obesity, or various combinations of the same.

At step 210, if the user selects BMI, for example, the system 100 provides them a list of locations based on their proximity as defined above of all providers e.g., Physician's offices, health clubs, fitness centers, etc., that provide an assessment for BMI. Likewise, if they have selected Body Fat Percentage (BFP) as their option of the metric they want to use for their assessment, they are provided a list of all the locations, e.g., physician's offices, health clubs, fitness centers, etc., which have the necessary equipment to provide BFP. For other choices, which include a blood test or other measurement, the system 100 likewise provides the user a list of the facilities based on vicinity and ability to provide these health metrics.

The individual can also set up an appointment with the location and on arrival is identified using a profile picture and printed bar code or QR code that identifies them, or the same is on their cell phone to show to the personnel at the center who scan it or take a picture of it, which then pre-populates the individual members information into the system. Forms of identification such as a driver's license can be used to further ensure the identity of the individual and match it with the profile.

The center personnel then proceed with the required measurements for the health metric e.g., BMI, BFP etc., such as measuring height, weight, body fat, etc. which they enter into the online system. For blood tests or other health metrics that require further assessment for example at a lab, the results are populated into the system 100 for processing at a later time.

The individual is encouraged to use the same measurement scale each time for determining their health metric for comparison purposes of one measurement with another at a different time. All health metrics, e.g. BMI, BFP etc., are calibrated with each other so each range for one method of measurement equivalent to the other so when the same is input into the system with the algorithm to calculate the proactivity score, the score generated is the same regardless of the metric used, e.g. BMI compared BFP etc.

At step 214, the user's supplied information and the information measured and collected at the participating center is stored in the database. At step 216, the system 100 uses this information and the score algorithm to generate, store, and display the user's proactivity score for health e.g., in the case of obesity, the proactivity score for weight management; similarly in the case of diabetes, the proactivity score for diabetes management. Based on the permission the user has selected, the score (a numeric value only, HIPAA compliant with no personal health information such as weight etc.) can be shared with different entities that have signed up with the system to have access to receiving the score, such as hospitals, physician's office, employers, life insurance providers, health insurance providers, and various other entities in the market place.

Figure 4:
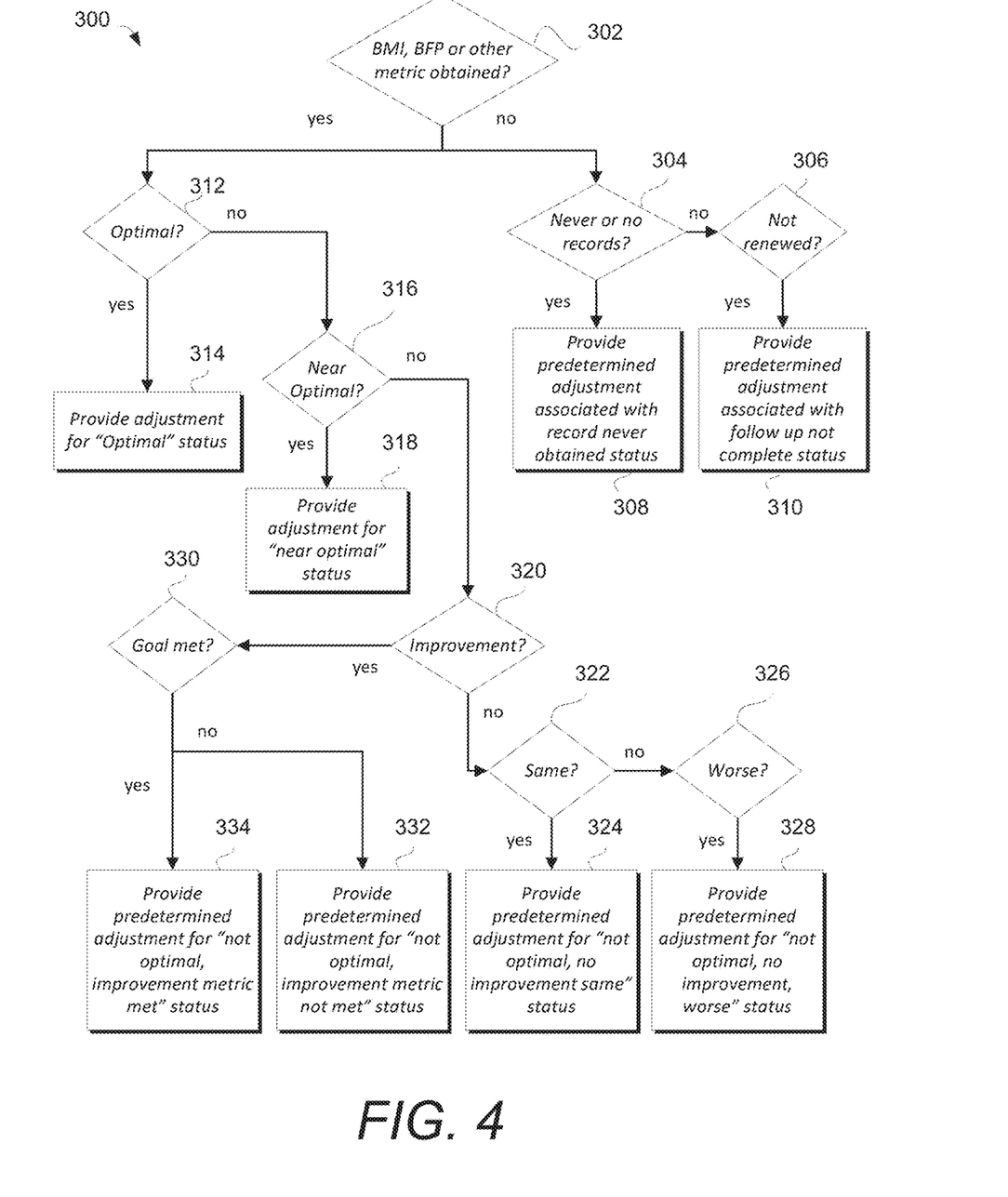
FIG. 4 shows a first exemplary process for generating, in part, a user's proactivity score, in accordance with the present disclosure.

FIG. 4 shows an exemplary process 300 for generating, in part, a user's proactivity score for health when BMI is used. Other health metrics used would work in a similar fashion. As described herein above, results of process 300 may be used to contribute to the overall user's proactivity score for health in a cumulative/additive manner. The process is initiated at step 302 where the system inquires whether a BMI, BFP, or similar health metric has been assessed within a certain time period in the immediate past. If no BMI or other health metric was currently obtained, the system inquiries, at step 304, whether any evaluation associated with the user has ever been recorded within the system 100. If an evaluation has been recorded, the system 100 inquiries whether an evaluation was just not renewed e.g., an up-to-date evaluation with a defined time period, such as a year at step 306. If a health metric has never been recorded, the process 300 contributes a predefined quanta to the overall score associated with the 'record-never-obtained' status of the user's BMI health metric 308. If a health metric is not renewed for follow up comparison before a set time period, e.g. one year, then the process 300 contributes a different predefined quanta to the overall score associated with the 'record-not-complete' status of the user's BMI health metric, e.g. user's score decays over the next two years if non-renewal continues and their score was in the optimal or near optimal range initially; if non-renewal continues but their score was not optimal or near optimal, they get a lower predefined quanta. If the obesity-based, e.g., BMI, BFP, or similar, health metric has been currently obtained, the process inquiries into the results at step 312. If the results correspond to an optimal range, the process 300 contributes a predefined quanta to the overall score associated with the 'optimal' status of the user's obesity-based health metric 314. If the results do not correspond to an optimal range, the process 300 inquires as to whether the results are a predefined amount from an optimal threshold 316. If the results correspond to a 'near-optimal' range, the process 300 contributes a predefined quanta to the overall score associated with the 'near-optimal' status of the user's obesity-based health metric 318.

If the obesity-based health metric does not correspond to a 'near-optimal' range, the process inquires whether there has been an improvement in the user's obesity-based health metric 320 from the last recorded previous measurement. If there has been no improvement in the user's obesity-based health metric, the process 300 inquires as to whether the obesity-based health metric is the same 322. If the obesity-based health metric is the same, the process 300 contributes a predefined quanta associated with a 'not-optimal, no improvement, same status' to the overall score. If the obesity-based health metric is not the same, the process inquiries as to whether it is worse 326. If the obesity-based health metric is worse the process 300 contributes a predefined quanta associated with a 'not-optimal, no improvement, worse status' to the overall score 328.

If there has been an improvement in the user's obesity-based health metric, the process 300 inquires as to whether a goal associated with the user has been met 330. If the user's obesity-based health metric shows that the goal has not been met, the process 300 contributes a predefined quanta associated with a 'not-optimal-improvement-goal-not-met' status to the overall score 332. If the user's obesity-based health metric shows that the goal has been met, the process 300 contributes a predefined quanta associated with a 'not-optimal-improvement-goal-met' status to the overall score 334.

Figure 5:
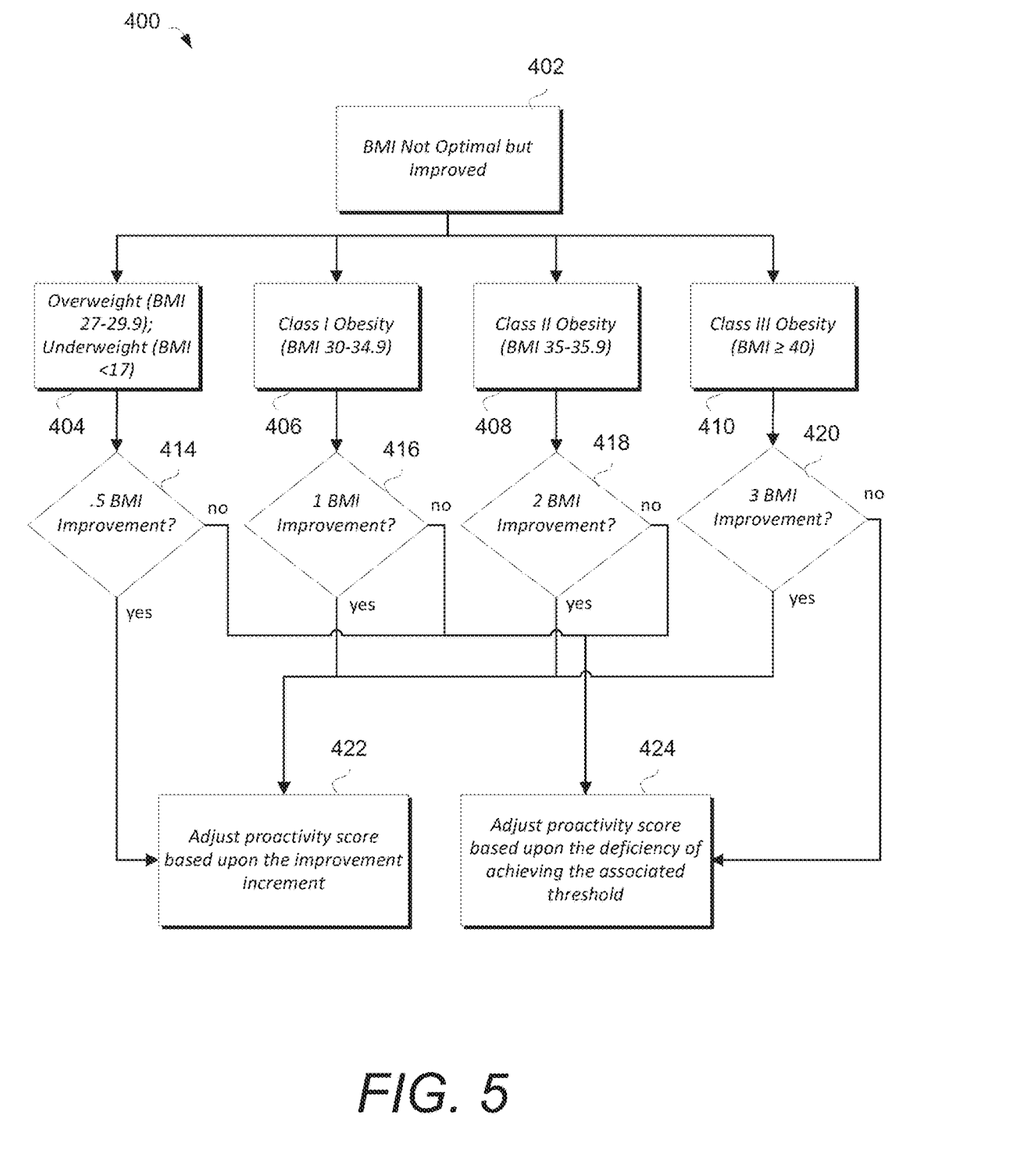
FIG. 5 shows a second exemplary process for generating, in part, a user's proactivity score, in accordance with the present disclosure.

FIG. 5 shows an exemplary process 400 for generating, in part, a user's proactivity score for health when a user does not have an optimal or near optimal health metric. The process is initiated at step 402 where the system 100 executes further evaluation of a user having a non-optimal or non-near optimal BMI, BFP, or other obesity-based health metric, but having an improvement from a prior value of that health metric. The process 400 includes processing the improvements based upon the latest data available on the user from a previous measurement associated with the user.

Used herein, as an example when the BMI health metric is used, the term "overweight" is defined as the condition wherein the individual has a BMI greater than or equal to 27 $kg/m^2$ and less than 30 $kg/m^2$ (404). The terms "overweight" and "pre-obese" are used interchangeably within various medical literature. The terms "obesity" or "being obese" and the like are defined as the condition wherein the individual has a BMI equal to or greater than 30 $kg/m^2$. According to a WHO definition the term obesity may be categorized as follows: the term "class I obesity" is the condition wherein the BMI is equal to or greater than 30 $kg/m^2$ but lower than 35 $kg/m^2$ (406); the term "class II obesity" is the condition wherein the BMI is equal to or greater than 35 $kg/m^2$ but lower than 40 $kg/m^2$ (408); the term "class III obesity" is the condition wherein the BMI is equal to or greater than 40 $kg/m^2$ (410). Just like BMI, other health metrics, such as BFP, waist circumference, waist to hip ratio etc. can be used in a similar fashion or in combination with other health metrics, such as those obtained through a blood test, with each calibrated to the rest so that measurements and the ranges correspond as much as possible across evaluation techniques.

Allocation of the user's overall proactivity score based upon the improvement is thereby related to the user's BMI, BFP, etc. classification 422. In one embodiment, a user associated with the overweight classification (404) must have at least a 0.5-point improvement in their BMI health metric from their previous measurement over a specified time period, such as a year, to receive an adjustment of a first quanta based upon the improvement (414). In one embodiment, a user associated with the class I obesity classification (406) must similarly have at least a 1-point improvement in their BMI health metric from their previous measurement over a specified time period, such as a year to receive an adjustment of a first quanta based upon the improvement (416). In one embodiment, a user associated with the class II obesity classification (408) must have at least a 2-point improvement in their BMI health metric from their previous measurement over a specified time period, such as a year, to receive an adjustment of a first quanta based upon the improvement (418). In one embodiment, a user associated with the class III obesity classification (410) must have at least a 3-point improvement in their BMI health metric from their previous measurement over a specified time period, such as a year, to receive an adjustment of a first quanta based upon the improvement (420). Users who have an improvement, but who have not met the thresholds associated with their respective BMI classifications have their overall score adjusted accordingly, for example with a score that is lower than the score designated for someone who has met the corresponding improvement threshold 424. Similar algorithms are used for other health metrics assessed if they have been incorporated into the score e.g., changes over time in Blood Pressure, Lipid Profile, Fasting Blood Sugar etc.

Figure 6:
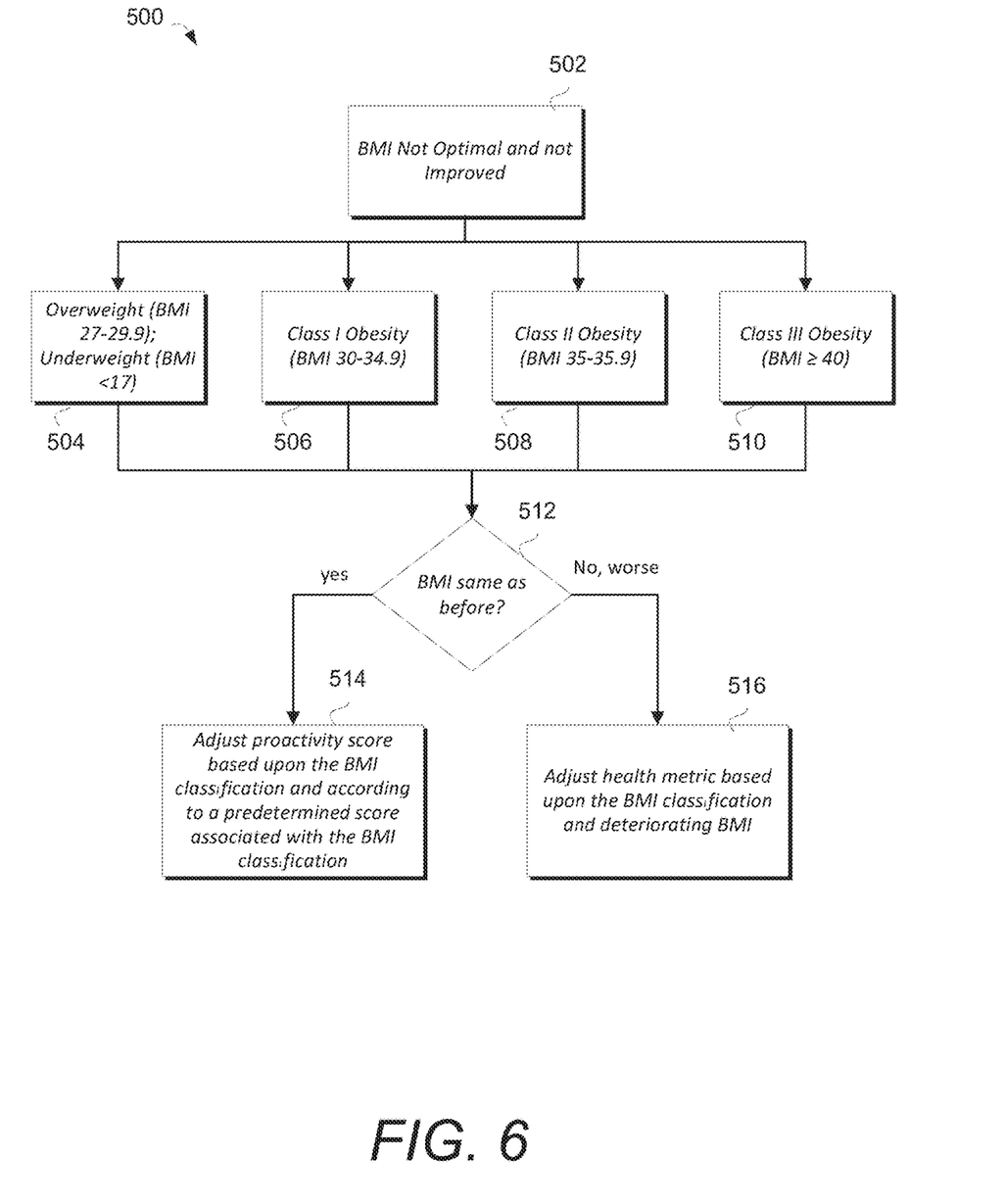
FIG. 6 shows a third exemplary process for generating, in part, a user's proactivity score, in accordance with the present disclosure.

FIG. 6 shows an exemplary process 500 for generating, in part, a user's proactivity score for health. As described herein above, results of process 500 may be used to contribute to the overall user's score in a cumulative/additive manner. The process is initiated at step 502 where the system 100 executes further evaluation of a user having a non-optimal BMI health metric and having no improvement from a prior BMI health metric. The process 500 includes processing the BMI health metric based upon a BMI classification associated with the user as described previously.

In one embodiment, for a user associated with the overweight classification (504), the process 500 determines whether the BMI health metric is the same as before 512. If the BMI health metric is the same, the system 100 adjusts the user's overall score by a predefined quanta associated with the results 516. If the BMI evaluation is worse, the system 100 adjusts the user's overall score a predefined quanta (e.g., lower than the allocation for "same"), associated with the results 514.

In one embodiment, for a user associated with the class II obesity classification (508), the process 500 determines whether the BMI health metric is the same as before 512. If the BMI health metric is the same, the system 100 adjusts the user's overall score by a predefined quanta associated with the results 516. If the BMI health metric is worse, the system 100 adjusts the user's overall score by a predefined quanta associated with the results 514.

In one embodiment, for a user associated with the class III obesity classification (510), the process 500 determines whether the BMI health metric is the same as before 512. If the BMI health metric is the same, the system 100 adjusts the user's overall score by a predefined quanta associated with the results 516. If the BMI health metric is worse, the system 100 adjusts the user's overall score by a predefined quanta associated with the results 514.

Adjustment of the user's overall score based upon the worsening BMI (or BFP, etc.) condition or non-improvement is related to a comparison with the user's BMI classification 514 and 516 from previous measurement at a specified time. In various embodiments, the quanta contributed that is associated with a worsening condition is less than the quanta contributed to the overall health metric associated with a BMI (or BFP, etc.) health metric that is the same.

Figure 7:
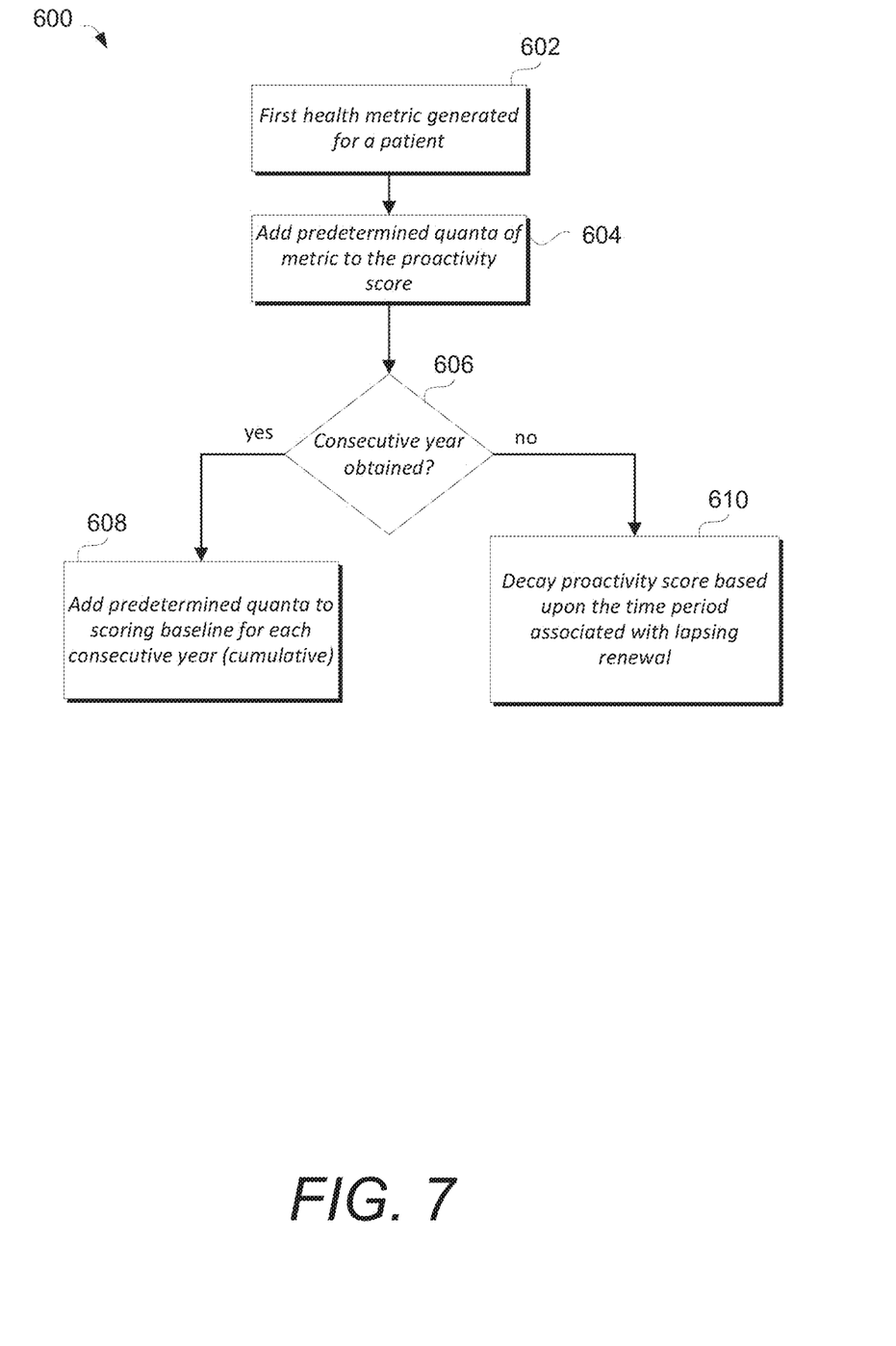
FIG. 7 shows a fourth exemplary process for generating, in part, a user's proactivity score, in accordance with the present disclosure.

FIG. 7 shows an exemplary process 600 for generating, in part, a user's overall proactivity score for health. As described herein above, results of process 600 may be used to contribute to the overall user's score in a cumulative/additive manner. The process is initiated at step 602 where the system 100 recalls a user's prior score. In one embodiment, the prior score is from a previous year or other periodic report which has been met. Upon the generation of the current score, the process contributes an additional predefined quanta to the overall score that is a percentage of the immediate past score 604.

The process 600 inquiries whether an evaluation has been made in consecutive years or other defined periodic time 606. If an evaluation has been made in consecutive years or other defined periodic time, the system 100 adjusts the user's overall score a predefined quanta associated with the occurrence 608 e.g., 5% of the previous year's score is added to the current one. If an evaluation has not been made in consecutive years or other defined periodic time, the system 100 inquires if the last score was in the optimal or near optimal range 610. If the last score was in the optimal or near optimal range, the previous score decreases by a certain quanta e.g., 10%, to become the new score for that year. The same inquiry is made in subsequent years and if non-renewal continues and the ranges are within optimal/near optimal, each year sees a decrease of certain quanta e.g., 10% from previous year which is allocated as the new score, up to a certain maximum e.g., 2 years. If non-renewal is greater than the defined time period e.g., 2 years, score decreases to a lower quanta plus a certain percentage of the previous year's score e.g., 100+5% from previous year. In one embodiment, the system is configured to decay a user's proactivity score based upon the time period associated with lapsing renewal. For example, by 10% each year missed or by a lesser amount In this way, a user's overall score is advantageously affected by having yearly or other periodic evaluations made. In one embodiment, having yearly or other periodic evaluations contributes to a higher baseline associated with the overall score. Similarly, if health metric evaluations are not done within a year, score decreases by a certain quanta e.g., 10% each year, up to maximum non-renewal period e.g., 2 years, at which time score drops to a certain quanta e.g., 100.

As mentioned, elements of the proactivity score can be cumulative/additive, e.g., various selective and obligatory algorithms may be executed to contribute quanta to the user's score. For example, an algorithm can be executed related to the sex or age of the user, e.g., if female, additional quanta may then be added to the user's score based upon results of the algorithm. Similarly, if the user's age is at a particular level e.g., ≥60, certain quanta calculated using the age e.g., 2 times age added to score, may be added to the user's score based upon the results of the algorithm. Other adjustment quanta can be included in algorithm as appropriate.

Figure 8:
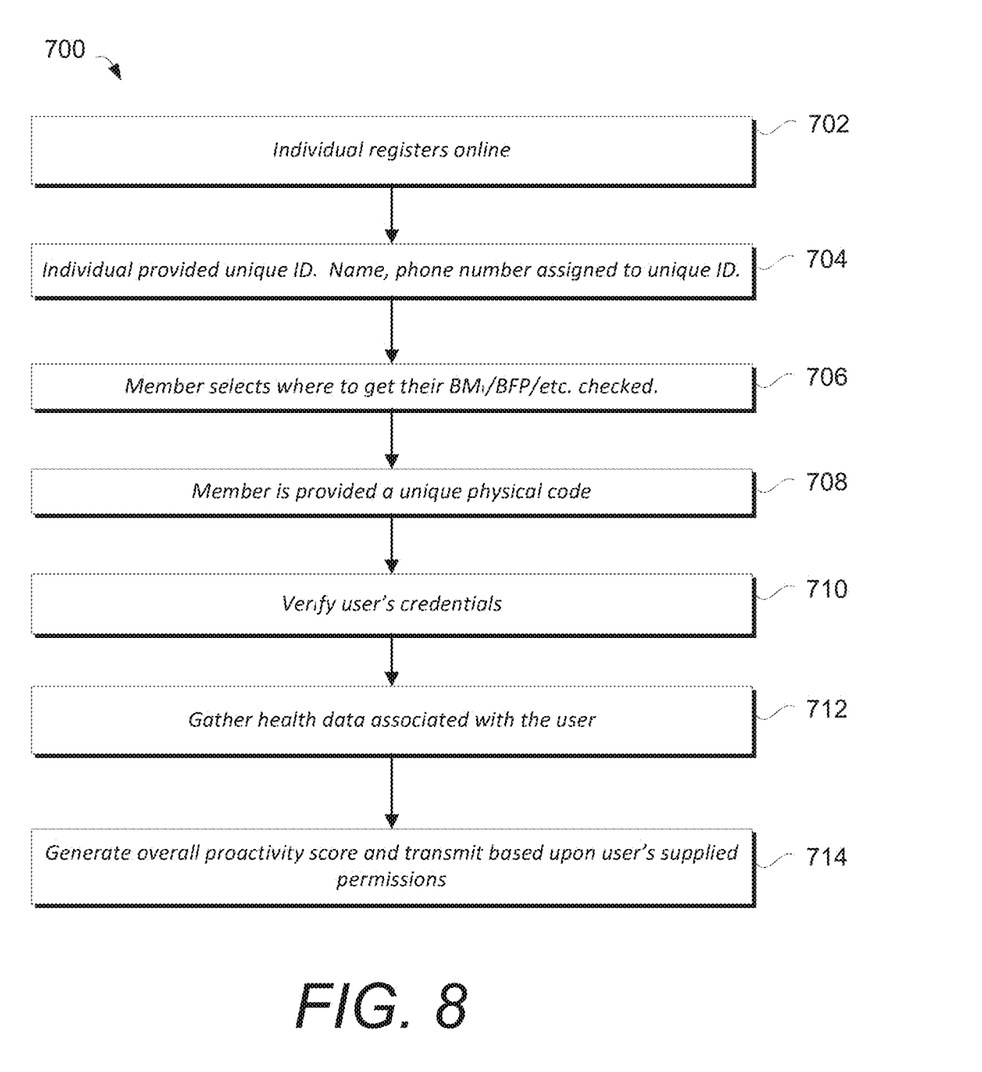
FIG. 8 shows an exemplary overall control flow diagram illustrating an exemplary process for determining the proactivity score from the perspective of an individual user, in accordance with the present disclosure.
Figure 9:
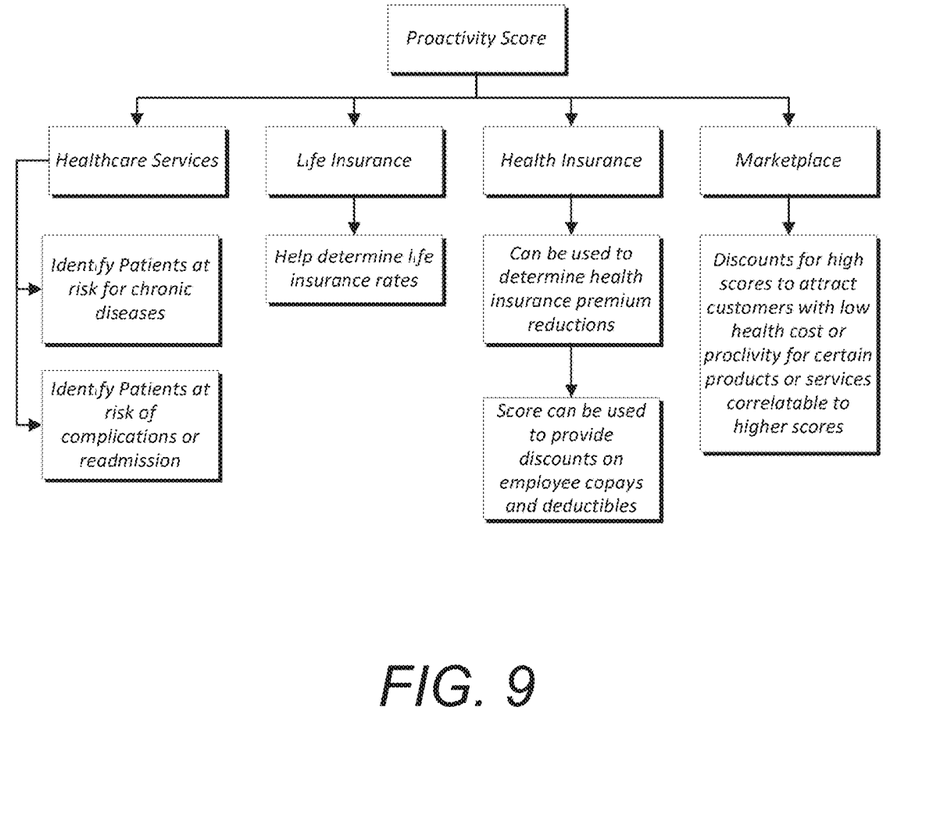
FIG. 9 shows various exemplary uses for the proactivity score, in accordance with the present disclosure.
Figure 10:
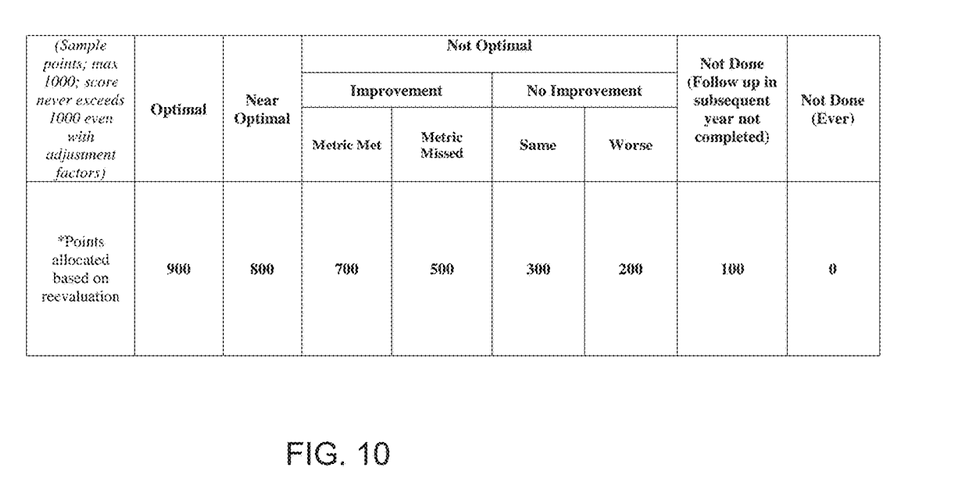
FIG. 10 shows a table of exemplary proactivity scores related to various health metrics and score evaluation execution, in accordance with the present disclosure.

FIG. 8 shows an exemplary overall control flow diagram illustrating an exemplary process 700 for determining the proactivity score from the perspective of an individual user. As FIG. 8 shows, the process 700 is initiated at step 702 by a user registering with the system 100. Registration may be executed by the individual-user online over the network 50 using any one of a number of devices, e.g., the mobile device or a computing device. In one embodiment, registration includes the user supplying personal information including, e.g., demographic-based information and contact information, e.g., email address, phone number, etc. A password or other security access means may be generated for the user.

At step 704, the user is provided or assigned a unique user identification. The identification may be a string of alphanumeric characters. The user's personal information and contact information is associated within the system 100 by the user identification. The system 100 is configured so that each user may access their information by logging in using their user identification or personal email address and secure password.

Upon successful registration, the user is prompted or direct to information associated with obtaining a BMI or BFP or other health metric 706. The information may include a physical address associated with a professional medical service facility, health club, fitness center or other locations.

In one embodiment, the user is provided a unique physical code, e.g., bar code, Quick Response (QR) Code linked to their profile to take to the facility 708. In one embodiment, a user's mobile device is linked to the user's profile. In this way, GPS location can corroborate that the intended user has correctly checked into center in order to get their BMI/BFP/etc. measured. In one embodiment, GPS location information is utilized for verification purposes. In one embodiment, the online profile includes a user's picture for identification purposes at the participating facility.

At step 710, the provided unique physical code is scanned or otherwise uploaded into the system 100 at the participating facility. In various embodiments, medical services personnel have their own login portal as an affiliate where they can verify member arrival. In one embodiment, services personnel can use a mobile device to take a picture of the member's printed bar code/QR code or of the code on the member's mobile device or scan it for the user's profile to pop up including picture which is validated with a driver's license or other photographic identification of the user to verify person and associated account.

Upon verification of the individual, the partner facility service personnel may gather data associated with user 712. Gathering data may include taking various measurements of the individual, e.g., height, weight, body fat %, waist, hip, neck measurements etc. This data is entered into the system 100 and associated with the user's system identification.

Upon proper entering of the health metric data, the system 100 may then determine a user's overall proactivity score based on the algorithms in the system 714. In one embodiment, all the information entered is used to calculate the overall score for the user. The overall score may then be populated into all appropriate portals based on member's permission settings e.g., to a user's portal for them to view or share, users may choose to send to their physician, or to their employer portal to provide premium discounts, for life insurance portal to provide discount for life insurance, and for health insurance portal to provide discount on health insurance.

In various embodiments, the system 100 may include functionality for various additional measurements associated with a user including measurements associated with, e.g., blood tests as well as exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity, as well as for various disease management, such as diabetes, hypertension etc. The term "visceral obesity" is defined as the condition wherein a waist-to-hip ratio of greater than or equal to 1.0 in men and 0.8 in women is measured. It defines the risk for insulin resistance and the development of pre-diabetes. The term "abdominal obesity" is usually defined as the condition wherein the waist circumference is >40 inches or 102 cm in men, and is >35 inches or 94 cm in women.

The disclosure has described certain preferred embodiments and modifications thereto. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A method for determining a health proactivity score of a human, comprising steps of:
   receiving, into a computing device at a first instance, a first set of at least two characteristics associated with the human, wherein the at least two characteristics are selected from the group consisting of a height, a weight, a percentage of body fat, a waist circumference, a waist and hip ratio, and a neck size, and
   wherein the at least two characteristics associated with the human are measured at a clinical center based on an appointment;
   calculating, by the computing device, a first value of a health-related metric based upon the first set of the at least two characteristics received at the first time instance;
   receiving, into the computing device at a second time instance, a second set of the at least two characteristics associated with the human;
   calculating, by the computing device, a second value of the health-related metric based upon the second set of the at least two characteristics received at the second time instance;
   storing, in a database, the first set of the at least two characteristics, the second set of the at least two characteristics, the first value of the health-related metric, and the second value of the health-related metric;
   determining, by the computing device, a change between the second value of the health-related metric and the first value of the health-related metric;
   determining, by the computing device, a category for the second value of the health-related metric from a plurality of pre-defined categories, wherein each pre-defined category is associated with a pre-defined range of a plurality of values of the health-related metric;
   dynamically determining, by the computing device, an overall proactivity score of the human based upon (1) the determined category and, (2) the change between the second value of the health-related metric and the first value of the health-related metric, wherein the overall proactivity score increases in response to improvement of health of the human;
   storing, in the database, the overall proactivity score of the human;
   automatically decaying, by the computing device, the overall proactivity score over time based on both a lapse of pre-defined time period in response to no further reception of the at least two characteristics at a third time instance, wherein the third time instance is subsequent to both the first time instance and the second time instance and a current value of the health-related metric; wherein the decaying is executed from the predefined time period away from a date associated with the calculating of the second health-related metric; and
   displaying, by the computing device, on a display of the computing device, the overall proactivity score.

2. The method of claim 1, wherein the overall proactivity score is decayed 10% over a year from the date associated with the calculating of the second value of the health-related metric.

3. The method of claim 1, further comprising:
defining a plurality of categories associated with various values of the health-related metric; and
adjusting the overall proactivity score based upon a category corresponding to the health-related metric.

4. The method of claim 3, further comprising:
associating, by the computing device, separate, predefined scoring increases and reductions in the overall proactivity score for each category; and
further adjusting, by the computing device, the overall proactivity score based upon the improvements and reductions associated with the category corresponding to the health-related metric associated with the human.

5. The method of claim 4, wherein a first increase is made to the overall proactivity score for a first category when the generated health-related metric associated with the human corresponds to a predefined improvement compared to a prior generated health-related metric associated with the human.

6. The method of claim 4, wherein a first reduction is made to the overall proactivity score for a first category when the generated health-related metric associated with the human corresponds to a predefined regression compared to a prior generated health-related metric associated with the human.

7. The method of claim 4, further comprising:
further adjusting the overall proactivity score based upon a percentage change of the health-related metric from a prior generated health-related metric of the human.

8. The method of claim 1, further comprising:
further adjusting the overall proactivity score in a linear manner based upon a percentage change of the health-related metric from a prior generated health-related metric of the human.

9. The method of claim 1, further comprising:
further adjusting the overall proactivity score based upon additional characteristics associated with the human including sex and age.

10. The method of claim 1, further comprising: determining a baseline associated with a first determined overall proactivity score and determining a second overall proactivity score based upon the baseline.

11. The method of claim 1, wherein the health-related metric is determined based upon obesity-related information associated with the human selected from one of a body mass index evaluation, a body fat percentage evaluation, a height and a weight, a waist circumference, a waist and hip ratio, a neck size, a skin fold thickness, a bio-electric impedance, a blood pressure measurement, a lipid profile, a blood glucose measurement, and a Hemoglobin measurement.

12. A health assessment system, comprising:
a processor;
a network interface;
memory storing an executable application, whereby execution of the application by the processor:
obtains at a first instance a first set of at least two physical characteristics associated with a human,
wherein the at least two characteristics are selected from the group consisting of a height, a weight, a percentage of body fat, a waist circumference, a waist and hip ratio, and a neck size, and wherein the at least two characteristics associated with the human are measured at a clinical center based on an appointment;
calculates a first value of a health-related metric based upon the first set of the at least two characteristics received at the first instance;
obtains at a second instance a second set of the at least two characteristics associated with the human;
calculates a second value of the health-related metric based upon the second set of the at least two characteristics received at the second time instance;
determines a change between the second value of the health-related metric and the first value of the health-related metric;
determines a category for the second value of the health-related metric from a plurality of pre-defined categories, wherein each pre-defined category is associated with a pre-defined range of a plurality of values of the health-related metric;
dynamically determine an overall proactivity score of the human based upon (1) the determined category and, (2) the change between the second value of the health-related metric and the first value of the health-related metric, wherein the overall proactivity score increases in response to improvement of health of the human;
automatically decays the overall proactivity score over time, based on both a pre-defined time period lapse in response to no further reception of the at least two characteristics at a third time instance, wherein the third time instance is subsequent to both the first time instance and the second time instance and a current value of the health-related metric; wherein the decaying is executed from the predefined time period away from a date associated with the calculating of the health-related metric; and
displays, on a display of the system, the overall proactivity score; and
a database for storing the first value of the health-related metric, the second value of the health-related metric, and the overall proactivity score of the human.

13. The system of claim 12, wherein the action further includes:
defining a plurality of categories associated with various values of the health-related metric, wherein a first category corresponds to a range of health-related metrics indicating better health of the human than a second category; and
adjusting the overall proactivity score based upon a category corresponding to the health-related metric, wherein the first category increases the overall proactivity score more than the second category.

14. The system of claim 13, wherein the action further includes:
associating separate, predefined scoring increases and reductions in the overall proactivity score for each category; and
further adjusting the overall proactivity score based upon the improvements and reductions associated with the category corresponding to the health-related metric associated with the human.

15. The system of claim 14, wherein a first increase is made to the overall proactivity score for the first category when the generated health-related metric associated with the human corresponds to a predefined improvement compared to a prior generated health-related metric associated with the human; and
wherein a first reduction is made to the overall proactivity score for the first category when the generated health-related metric associated with the human corresponds to a predefined regression compared to a prior generated health-related metric associated with the human.

16. The system of claim 14, wherein the action further includes:

further adjusting the overall proactivity score based upon a percentage change of the health-related metric from a prior generated health-related metric of the human, wherein the further adjusting is executed in a linear manner.

17. The system of claim 14, wherein the action further includes:

determining a baseline associated with a first determined overall proactivity score and determining a second overall proactivity score based upon the baseline, wherein the health-related metric is determined based upon obesity-related information associated with the human selected from one of a body mass index evaluation, a body fat percentage evaluation, a height and a weight, a waist circumference, a waist and hip ratio, a neck size, a skin fold thickness, a bio-electric impedance, a blood pressure measurement, a lipid profile, a blood glucose measurement, and a Hemoglobin measurement.

* * * * *